(12) United States Patent
Liu et al.

(10) Patent No.: US 10,874,807 B2
(45) Date of Patent: *Dec. 29, 2020

(54) COMBINED ULTRASONIC ATOMIZER, ATOMIZATION METHOD THEREOF AND ELECTRONIC CIGARETTE

(71) Applicant: CHINA TOBACCO HUNAN INDUSTRIAL CO., LTD., Hunan (CN)

(72) Inventors: Jianfu Liu, Hunan (CN); Kejun Zhong, Hunan (CN); Xiaoyi Guo, Hunan (CN); Wei Huang, Hunan (CN); Yuangang Dai, Hunan (CN); Xinqiang Yin, Hunan (CN); Jianhua Yi, Hunan (CN); Hong Yu, Hunan (CN); Lizhou Shen, Hunan (CN)

(73) Assignee: China Tobacco Hunan Industrial Co., Ltd., Hunan (CN)

( * ) Notice: Subject to any disclaimer, the term of this patent is extended or adjusted under 35 U.S.C. 154(b) by 520 days.

This patent is subject to a terminal disclaimer.

(21) Appl. No.: 15/577,275

(22) PCT Filed: Jul. 18, 2016

(86) PCT No.: PCT/CN2016/090272
§ 371 (c)(1),
(2) Date: Nov. 27, 2017

(87) PCT Pub. No.: WO2018/000469
PCT Pub. Date: Jan. 4, 2018

(65) Prior Publication Data
US 2018/0318530 A1    Nov. 8, 2018

(30) Foreign Application Priority Data

Jun. 30, 2016 (CN) .......................... 2016 1 0498877

(51) Int. Cl.
*A61M 15/00* (2006.01)
*A24F 47/00* (2020.01)
(Continued)

(52) U.S. Cl.
CPC ......... *A61M 15/0085* (2013.01); *A24F 47/00* (2013.01); *A24F 47/002* (2013.01);
(Continued)

(58) Field of Classification Search
CPC ............ A61M 15/0085; A61M 11/001; A61M 11/042; A61M 15/0001; A61M 11/005;
(Continued)

(56) References Cited

U.S. PATENT DOCUMENTS 4,877,989 A * 10/1989 Drews ................. B05B 17/0623
310/323.01
5,515,842 A * 5/1996 Ramseyer ......... A61M 15/0085
128/200.14
(Continued)

FOREIGN PATENT DOCUMENTS

CN      204070578 U      1/2015
CN      204169066 U      2/2015
(Continued)

OTHER PUBLICATIONS

International Search Report issued in International Application No. PCT/CN2016/090272 dated Apr. 6, 2017, 5 pages.
(Continued)

*Primary Examiner* — Timothy A Stanis
*Assistant Examiner* — Jonathan S Paciorek
(74) *Attorney, Agent, or Firm* — Mauriel Kapouytian Woods LLP; Liang Huang; Michael Mauriel

(57) ABSTRACT

Embodiments of the invention disclose a combined ultrasonic atomizer, an atomization method thereof and electronic cigarette. The combined ultrasonic atomizer com-
(Continued)

Figure 1:
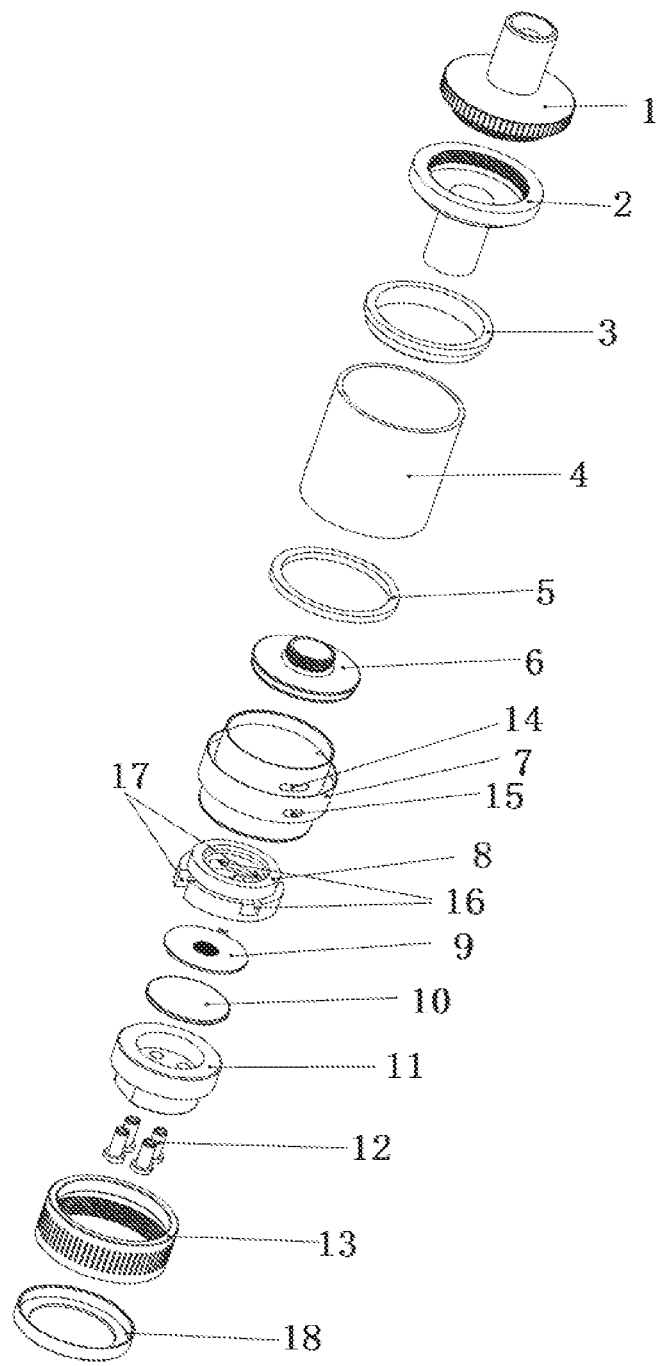
Figure 2:
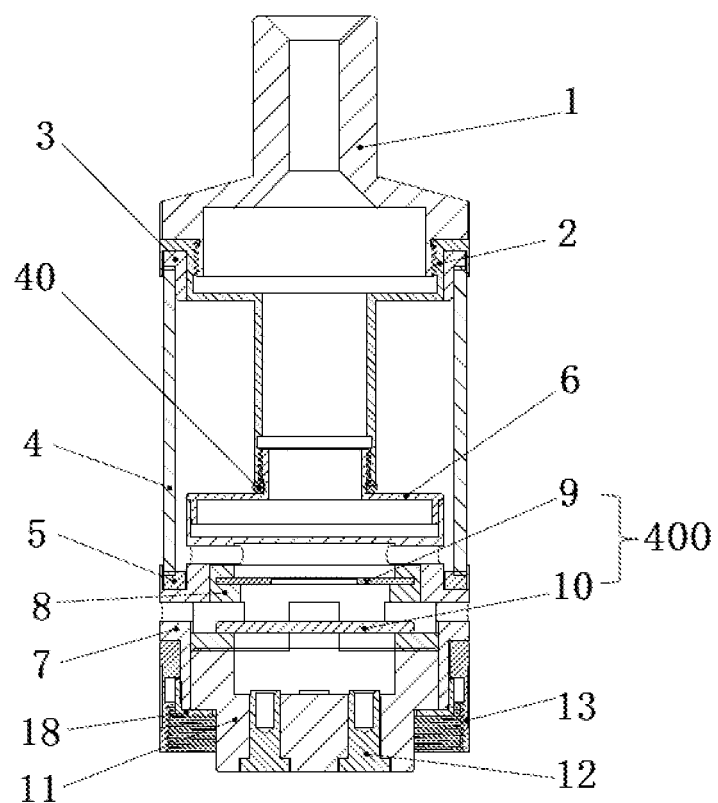

prises a tobacco tar bin, an air inlet passage, a tobacco tar smoke outlet passage and an atomization component; the atomization component comprises a micropore atomization piece used for performing first-stage oscillation atomization on tobacco tar and a high-frequency atomization piece used for performing second-stage oscillation atomization on the tobacco tar; the micropore atomization piece is communicated with a tobacco tar outlet of the tobacco tar bin by direct contact or through a tobacco tar guide structure, and an ejection end of the micropore atomization piece is aligned to an atomization surface of the high-frequency atomization piece; and the air inlet passage communicates with an atomization cavity located between the micropore atomization piece and the high-frequency atomization piece, and the atomization cavity communicates with the tobacco tar smoke outlet passage.

20 Claims, 14 Drawing Sheets

(51) Int. Cl.
  *A61M 11/00* (2006.01)
  *A61M 11/04* (2006.01)
  *B05B 17/06* (2006.01)
(52) U.S. Cl.
  CPC .......... *A24F 47/008* (2013.01); *A61M 11/001* (2014.02); *A61M 11/042* (2014.02); *A61M 15/0001* (2014.02); *B05B 17/06* (2013.01)
(58) Field of Classification Search
  CPC ....... A61M 15/06; A24F 47/00; A24F 47/008; A24F 40/00; A24F 40/05; A24F 40/20; B05B 17/06
  See application file for complete search history.

(56) References Cited

U.S. PATENT DOCUMENTS

| | | | | |
|---|---|---|---|---|
| 5,970,974 | A | * | 10/1999 | Van Der Linden .......................... A61M 15/0065 128/200.14 |
| 2010/0078013 | A1 | * | 4/2010 | Power ................. B05B 17/0646 128/200.18 |
| 2016/0089508 | A1 | | 3/2016 | Smith et al. |

FOREIGN PATENT DOCUMENTS

| | | |
|---|---|---|
| CN | 204317501 U | 5/2015 |
| CN | 204742639 U | 11/2015 |
| CN | 105266206 A | 1/2016 |
| CN | 105476071 A | 4/2016 |
| CN | 105559150 A | 5/2016 |
| CN | 105559151 A | 5/2016 |
| CN | 205757212 U | 12/2016 |
| EP | 3434120 A1 | 1/2019 |
| JP | 2001069963 A | 3/2001 |
| WO | 2016/026156 A1 | 8/2014 |

OTHER PUBLICATIONS

European Search Report, European Application No. 16886802.4, dated Feb. 14, 2019, 1 page.

* cited by examiner

COMBINED ULTRASONIC ATOMIZER, ATOMIZATION METHOD THEREOF AND ELECTRONIC CIGARETTE

CROSS REFERENCE TO RELATED APPLICATIONS

This application is a national phase application of international application number PCT/CN2016/090272 filed on Jul. 18, 2016, which claims priority to Chinese application number 2016104988777 filed on Jun. 30, 2016. The entire contents of these applications are hereby incorporated herein by reference.

TECHNICAL FIELD

The present invention relates to a combined ultrasonic atomizer, an atomization method thereof and an electronic cigarette, and the present invention belongs to the field of electronic cigarette products.

BACKGROUND ART

Currently, ultrasonic high-frequency atomizers on the market guide tobacco tar by using tobacco tar guide cotton, which is prone to the problem that atomization pieces are soaked in the tobacco tar or the supply of the tobacco tar is insufficient, namely the supply speed of tobacco tar is hard to control, resulting in that the high-frequency ultrasonic atomization pieces cannot work normally and are hard to make full play of the optimal atomization effect.

The existing ultrasonic high-frequency atomizers mainly rely on the tobacco tar guide cotton to guide the tobacco tar, therefore the tobacco tar guide speed is hard to control, and it is easy to produce the phenomenon that the atomization pieces are soaked in the tobacco tar caused by over fast supply of the tobacco tar or the supply of the tobacco tar is insufficient, such that the atomization pieces cannot atomize smoke; even if the tobacco tar control rate is suitable, the atomized smoke needs to penetrate through the tobacco tar guide cotton to be inhaled by a human body, and when the smoke penetrates through the tobacco tar guide cotton, particles will become larger, and the smoke is weakened; in addition, in the case of smoking training, a cotton burning phenomenon is easily to appear in the case of insufficient supply of the tobacco tar of the atomization pieces, thereby affecting the taste of the smoke; and meanwhile, due to the dry burning of the tobacco tar guide cotton, burnt flavor or peculiar smell is produced easily, and even harmful substances are produced to harm the health of users. Finally, the tobacco tar guide cotton takes away a lot of heat, resulting in hot cigarette bodies, low heat efficiency, slow atomization start speed and other undesirable phenomena.

The Chinese patent CN201610145881.5 discloses an electronic cigarette atomizer and electronic cigarette. The atomizer comprises a suction nozzle and a tobacco tar storage cavity, and an atomization cavity is provided between the tobacco tar storage cavity and the suction nozzle for connecting; the atomization cavity is formed by covering an upper cover on a bottom cover; a first heating body is fixed in the atomization cavity; the first heating body is in contact with a tobacco tar storage piece; the tobacco tar storage piece is in contact with the top end of a tobacco tar guide structure in the tobacco tar storage cavity; and at least one air outlet hole communicated with a suction nozzle cavity is provided in the upper cover. The first heating body atomizes liquid into smoke in a working process, at the same time, the air in the atomization cavity is heated by the first heating body, so that the air in the atomization cavity is heated to expand, a high-temperature and high-pressure cavity body is formed in the atomization cavity at the moment, therefore the smoke is mixed with the heated air in the atomization cavity and then is automatically ejected from an air outlet hole; and since the smoke in the atomization cavity is mixed and atomized with the heated air, the taste of the smoke is fine and smooth.

The Chinese Patent CN201610160216.3 discloses an ultrasonic atomizer and electronic cigarette, the ultrasonic atomizer comprises an atomization piece and a liquid guide structure for guiding liquid onto the upper surface of the atomization piece; the liquid guide structure communicates with a liquid storage cavity; the upper surface of the atomization piece communicates with an airflow passage; and the atomization piece comprises a piezoelectric ceramic layer and an electric conductor for driving the piezoelectric ceramic layer to vibrate. There is no need to provide any micropore in the atomization piece for ejecting an atomized gas, thereby the situation that the atomized gas cannot be ejected because the micropore is blocked by larger particles of the atomized gas would not appear, and meanwhile the liquid leakage of the atomizer can be better prevented.

The two patents mentioned above are the previous research results by the applicant, but the defects of excessive tobacco tar supply or insufficient tobacco tar supply of the tobacco tar guide cotton still cannot be overcome.

Contents of Invention

The present invention aims at providing a combined ultrasonic atomizer, an atomization method thereof and an electronic cigarette. The atomizer supplies tobacco tar by atomization of an ultrasonic micropore atomization piece and atomizes the tobacco tar by an ultrasonic high-frequency atomization piece, and due to the combination of the ultrasonic micropore atomization piece and the ultrasonic high-frequency atomization piece, the defects of excessive tobacco tar supply or insufficient tobacco tar supply of the traditional tobacco tar guide cotton can be overcome.

To achieve the above-mentioned objective, the present invention adopts the technical solutions as follows:

A combined ultrasonic atomizer comprises a tobacco tar bin, an air inlet passage, a tobacco tar smoke outlet passage and an atomization component; its structural features are as follows: the atomization component comprises a micropore atomization piece used for performing first stage oscillation atomization on tobacco tar and a high-frequency atomization piece used for performing second stage oscillation atomization on the tobacco tar; the micropore atomization piece is communicated with a tobacco tar outlet of the tobacco tar bin by direct contact or through a tobacco tar guide structure, and an ejection end of the micropore atomization piece is aligned to an atomization surface of the high-frequency atomization piece; and the air inlet passage communicates with an atomization cavity located between the micropore atomization piece and the high-frequency atomization piece, and the atomization cavity communicates with the tobacco tar smoke outlet passage.

Therefore, in the present invention, a certain amount of tobacco tar is ejected using the ultrasonic micropore atomization piece to supply the tobacco tar, and then a proper amount of tobacco tar is atomized by the high-frequency atomization piece, the supply speed of the tobacco tar of this structure is controllable and accurate, in addition, the high-frequency atomization piece is not in direct contact with the tobacco tar guide cotton, so the cotton burning or tobacco tar soaking caused by insufficient tobacco tar supply or too fast tobacco tar supply speed can be avoided, and the negative effects caused by the tobacco tar guide using the tobacco tar guide cotton traditionally can be solved.

According to embodiments of the present invention, the present invention can be further optimized, and the following technical solutions are formed after the optimization:

The micropore atomization piece and the high-frequency atomization piece are fixed to a silica gel base, and an air inlet hole or an air inlet groove communicated with the air inlet passage is provided in the silica gel base, and an air outlet hole or an air outlet groove communicated with the tobacco tar smoke outlet passage is provided in the silica gel base.

An outlet end of the tobacco tar smoke outlet passage communicates with a suction nozzle base.

The aperture of the micropore atomization piece is 40-100 microns, and the atomization surface of the high-frequency atomization piece is of solid structure.

The micropore atomization piece and the high-frequency atomization piece are horizontally provided below the tobacco tar bin, and the micropore atomization piece is located between the high-frequency atomization piece and the tobacco tar bin; and the tobacco tar outlet of the tobacco tar bin directly communicates with the upper end face of the micropore atomization piece.

An air corridor for communication the upper end with the lower end is provided at the central position of the tobacco tar bin, the air corridor communicates with the atomization cavity to form the tobacco tar smoke outlet passage.

The lower end of the tobacco tar bin is connected with a base, and the silica gel base for fixing the micropore atomization piece and the high-frequency atomization piece is installed in the base; the base is provided with a tobacco tar inlet hole and an air inlet hole, and an air inlet groove and an air outlet groove are provided in the silica gel base; and the air inlet hole in the base correspondingly communicates with the air inlet groove in the silica gel base to form the air inlet passage.

The lower end of the base is connected with an insulating base, and an electrode ring is installed on the insulating base, and the micropore atomization piece and the high-frequency atomization piece are respectively in electrical connection with the electrode ring through conducting wires.

The micropore atomization piece and the high-frequency atomization piece are horizontally provided above the tobacco tar bin, and the micropore atomization piece is located between the high-frequency atomization piece and the tobacco tar bin; and the tobacco tar outlet of the tobacco tar bin communicates with the lower end face of the micropore atomization piece through tobacco tar guide cotton. Therefore, the high-frequency atomization piece is provided above the micropore atomization piece, small-particle smoke is taken away to be inhaled by a user, and the large-particle smoke droplets are dropped onto the micropore atomization piece to be ejected to the high-frequency atomization piece again for secondary high-frequency atomization, and thus the taste of the smoke is further improved.

A connecting ring for communicating the upper with the lower ends is provided at the central position of the tobacco tar bin, the tobacco tar guide cotton is provided in the connecting ring, and the tobacco tar guide cotton is provided at the top end of the connecting ring; and a plurality of tobacco tar pass holes are provided in the wall surface of the connecting ring.

An upper end cover is installed at the top end of the tobacco tar bin, and the silica gel base for fixing the micropore atomization piece and the high-frequency atomization piece is installed in the upper end cover; the upper end cover is provided with an air inlet hole, and an air inlet hole and an air outlet groove are provided in the silica gel base; and the air inlet hole of the upper end cover correspondingly communicates with the air inlet hole of the silica gel base to form the air inlet passage.

The air outlet groove is provided in the top end of the side wall of the silica gel base, and the air outlet groove communicates with the atomization cavity to serve as the tobacco tar smoke outlet passage.

The micropore atomization piece and the high-frequency atomization piece are vertically provided on one side of the tobacco tar bin, and the micropore atomization piece is located between the high-frequency atomization piece and the tobacco tar bin; and the tobacco tar outlet of the tobacco tar bin communicates with the inner end face of the micropore atomization piece through tobacco tar guide cotton.

A mounting hole is provided in the side wall of the tobacco tar bin, and the silica gel base for fixing the micropore atomization piece and the high-frequency atomization piece is installed in the mounting hole; an air inlet hole and an air outlet hole are provided in the side wall of the silica gel base, and an air inlet groove and an air outlet groove are provided in the side wall of the tobacco tar bin; and the air inlet hole in the silica gel base correspondingly communicates with the air inlet groove in the tobacco tar bin to form the air inlet passage communicated with the atomization cavity, and the air outlet hole in the silica gel base correspondingly communicates with the air outlet groove in the tobacco tar bin to form the tobacco tar smoke outlet passage communicated with the atomization cavity.

The tobacco tar bin is provided in a housing, and an air inlet hole communicated with the air inlet groove in the tobacco tar bin is provided in the side wall of the housing.

Based on the same inventive conception, the present invention further provides an electronic cigarette, comprising a battery component and the above-mentioned combined ultrasonic atomizer; the battery component respectively supplies power to the micropore atomization piece and the high-frequency atomization piece.

The battery component comprises a battery, an insulating base installed at the top end of the battery, an electrode column and an electrode ring both installed in the insulating base which are conducted with the battery; and the electrode ring is in electrical connection with the micropore atomization piece and the high-frequency atomization piece through conducting wires respectively.

Based on the same inventive conception, the present invention further provides a method for atomizing tobacco tar by using the above-mentioned combined ultrasonic atomizer, comprising the following steps:

S1, transferring the tobacco tar in the tobacco tar bin onto the micropore atomization piece directly or through the tobacco tar guide structure to perform oscillation atomization;

S2, ejecting the tobacco tar on the micropore atomization piece after oscillation atomization onto the atomization surface of the high-frequency atomization piece to perform secondary atomization; and S3, transferring the tobacco tar smoke produced by the secondary atomization of the high-frequency atomization piece to the suction nozzle through the air outlet passage using the air entered from the air inlet passage of the ultrasonic atomizer.

In step S1, the aperture of the micropore atomization piece is 40-100 microns, the vibration frequency of the micropore atomization piece is 100-200 KHZ, and the particle size of the atomized tobacco tar smoke after atomization is 50-120 microns.

In step S2, the atomization surface of the high-frequency atomization piece is of solid structure, the vibration frequency of the high-frequency atomization piece is 1-3 MHZ, and the particle size of the atomized tobacco tar smoke after atomization is 70-130 nanometers.

In the present invention, the tobacco tar is supplied by the ejection of the ultrasonic micropore atomization piece, besides, through combination of the atomization of the ultrasonic high-frequency atomization piece, the electronic cigarette atomizer with reliable performance and excellent atomization effect is created.

The working principle of the present invention is as follows: in the present invention, the tobacco tar is ejected to the surface of the high-frequency atomization piece in a smoke-like shape using the atomization principle of the ultrasonic micropore atomization piece, as the smoke ejected by the micropore atomization piece belongs to large-particle smoke instead of the smoke produced by the so called heating atomization, the smoke obtained by atomization of the micropore cannot have the atomization taste of the traditional electronic cigarette, thus the large-particle smoke needs to be atomized by the high-frequency atomization piece into small-particle smoke, then the atomization effect of the traditional electronic cigarette can be achieved, and an air passage is provided between the two atomization pieces, so that the atomized smoke can be taken out; and moreover, as the tobacco tar is supplied by the spray of the micropore atomization piece, the amount of the tobacco tar supply can be well controlled, and the consistency of the supply quantity of each take can be guaranteed.

Compared with the prior art, the present invention has the following beneficial effects:

1. The automation has quick start speed, the atomization is sufficient, and the amount of the smoke is large.

2. The heat efficiency is high, the hot loss is small, energy and electricity are saved.

3. There is no cotton participated in the atomization of embodiment 1, thereby being free of the smell of burnt flavor or peculiar smell, and thus the taste is purer.

DESCRIPTION OF FIGURES

FIG. 1 is an explosive schematic diagram of an embodiment 1 of the present invention;

FIG. 2 is a schematic diagram of a longitudinal section structure of the embodiment 1 of the present invention;

FIG. 3 is a schematic diagram of a longitudinal section structure of a battery component of the present invention;

FIG. 4 is a schematic diagram (front sectional view) of air inflow and tobacco tar smoke outflow of the embodiment 1 of the present invention;

FIG. 5 is a schematic diagram (lateral sectional view) of air inflow and tobacco tar smoke outflow of the embodiment 1 of the present invention;

FIG. 6 is an oblique sectional view of the embodiment 1 of the present invention;

FIG. 7 is a schematic diagram of routing trace and electric conduction of the embodiment 1 of the present invention;

FIG. 8 is an explosive schematic diagram of an embodiment 2 of the present invention;

FIG. 9 is a schematic diagram of a longitudinal section structure of the embodiment 2 of the present invention;

FIG. 10 is a schematic diagram (front sectional view) of air inflow and tobacco tar smoke outflow of the embodiment 2 of the present invention;

FIG. 11 is a schematic diagram (lateral sectional view) of air inflow and tobacco tar smoke outflow of the embodiment 2 of the present invention;

FIG. 12 is an oblique sectional view of the embodiment 2 of the present invention;

FIG. 13 is a schematic diagram of routing trace and electric conduction of the embodiment 2 of the present invention;

FIG. 14 is an explosive schematic diagram of an embodiment 3 of the present invention;

FIG. 15 is a schematic diagram (front sectional view) of a longitudinal section structure of the embodiment 3 of the present invention;

FIG. 16 is a schematic diagram (lateral sectional view) of the longitudinal section structure of the embodiment 3 of the present invention;

FIG. 17 is a schematic diagram (lateral sectional view) of air inflow and tobacco tar smoke outflow of the embodiment 3 of the present invention;

FIG. 18 is a schematic diagram (front sectional view) of routing trace and electric conduction of the embodiment 3 of the present invention;

FIG. 19 is a schematic diagram (lateral sectional view) of routing trace and electric conduction of the embodiment 3 of the present invention.

In the above figures, 100 represents an air inlet passage, 200 represents a tobacco tar smoke outlet passage, 300 represents an atomization cavity, 400 represents an atomization component, 401 represents an air corridor, 211 represents a tobacco tar pass hole, and 50 represents a battery component.

SPECIFIC MODE FOR CARRYING OUT THE INVENTION

Hereinafter, the present invention will be described in detail with reference to the drawings and in combination with embodiments. It should be noted that the embodiments in the present invention and the features in the embodiments can be combined with each other without conflict. For the sake of convenience, the words "up", "down", "left" and "right" appear in the text below only express consistency with the upper, lower, left and right directions of the drawings, and do not constitute limitation to the structure.

Embodiment 1

As shown in FIG. 1, a combined ultrasonic atomizer comprises a suction nozzle base 1, an upper end cover 2, a tobacco tar bin 4, a sealing ring 3 provided between the upper end cover 2 and the tobacco tar bin 4, an atomization cover 6, a base 7, a silica gel base 8, an insulating base 11, a micropore atomization piece 9 and a high-frequency atomization piece 10 both provided between the silica gel base 8 and the insulating base 11, four electrode rings 12 and a locking ring 13 both installed on the insulating base 11, and a fixing ring 18 installed on the locking ring 13. As shown in FIG. 2, a sealing ring 40 is provided between the tobacco tar bin 4 and the atomization cover 6, and a sealing gasket 5 is provided between the tobacco tar bin 4 and the base 7.

As shown in FIG. 2, a tobacco tar inlet hole 14 and an air inlet hole 15 are both provided in the base 7, and an air inlet groove 16 and an air outlet groove 17 are both provided in the silica gel base 8. The air inlet hole 15 in the base 7 and the air inlet groove 16 in the silica gel base 8 are correspondingly provided. The suction nozzle base 1 is of hollow structure, and an air corridor 401 is provided at the middle of the tobacco tar bin 4. The air inlet hole 15, the air inlet groove 16, the air outlet groove 17, the air corridor 401 and a hollow passage of the suction nozzle base 1 communicate with each other in sequence.

As shown in FIG. 2, FIG. 4, FIG. 5, FIG. 6 and FIG. 7, the micropore atomization piece 9 and the high-frequency atomization piece 10 are both located at the bottom of the tobacco tar bin 4, and the micropore atomization piece 9 is located above the high-frequency atomization piece 10. In a working process, the tobacco tar in the tobacco tar bin 4 reaches to the surface of the micropore atomization piece 9 through the tobacco tar inlet hole 14 in the base 7, the tobacco tar is formed to a smoke shape (the particle size of the tobacco tar smoke is 50-120 microns) downwards and is ejected onto the upper surface of the high-frequency atomization piece 10 under the ultrasonic oscillation of the micropore atomization piece, the tobacco tar smoke is subjected to secondary atomization by the ultrasonic high-frequency oscillation of the high-frequency atomization piece 10, the particle size after the atomization is 70-130 nm, then the gas enters the upper surface of the high-frequency atomization piece 10 along the air inlet hole 15 in the base 7 and the air inlet groove 16 in the silica gel base 8; after passing through the air corridor 401 located at the middle of the tobacco tar bin 4 along the air outlet groove 17 in the silica gel base 8, the atomized tobacco tar smoke flows to the suction nozzle base 1 and is inhaled by a smoker.

In the embodiment, the tobacco tar is mainly supplied by the ultrasonic micropore atomization piece, and the tobacco tar is atomized by the high-frequency ultrasonic atomization piece; the two atomization pieces adopt flatwise structures, the atomization surfaces are opposite to each other, the micropore atomization piece is provided on the high-frequency atomization piece, the high-frequency atomization piece is provided below the micropore atomization piece, and the two atomization pieces are both located at the bottom of the tobacco tar bin 4; the micropore atomization piece ejects the tobacco tar onto the surface of the high-frequency atomization piece downward, and the high-frequency atomization piece atomizes the tobacco tar ejected by the micropore atomization piece; and the tobacco tar enters from the bottom of the atomizer, the air enters from the side face of the bottom, and the air is discharged from the center of the top.

In the embodiment, the aperture of the micropore atomization piece 9 is 40-100 microns, the vibration frequency thereof is 100-200 KHZ, the high-frequency atomization piece 10 is of solid structure, and the vibration frequency thereof is 1-3 MHZ.

When tobacco tar 39 needs to be injected in the tobacco tar bin 4, the base 7 can be unscrewed to inject the tobacco tar along the bottom of the wall of the tobacco tar bin 4.

Figure 3:
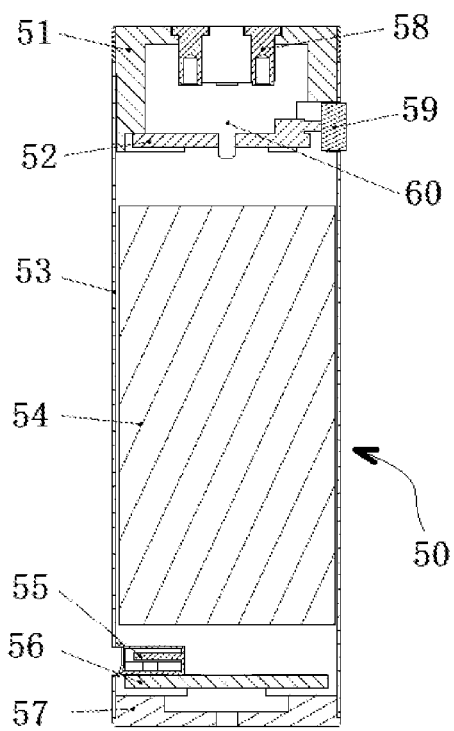
Figure 4:
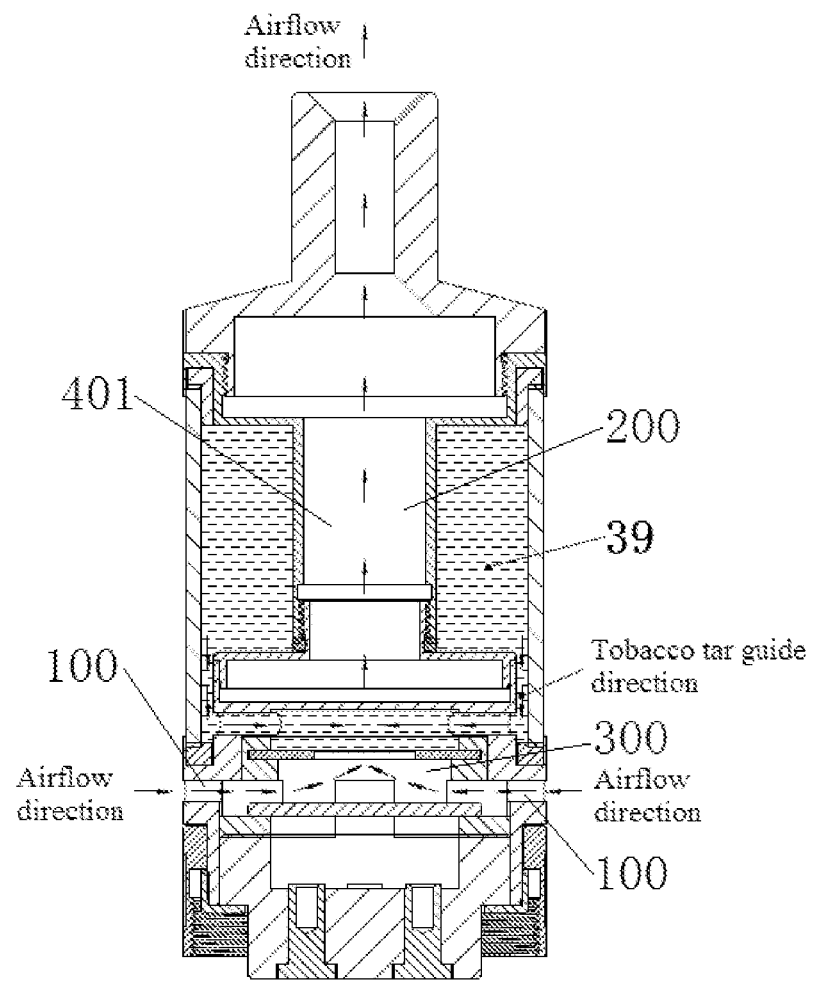
Figure 5:
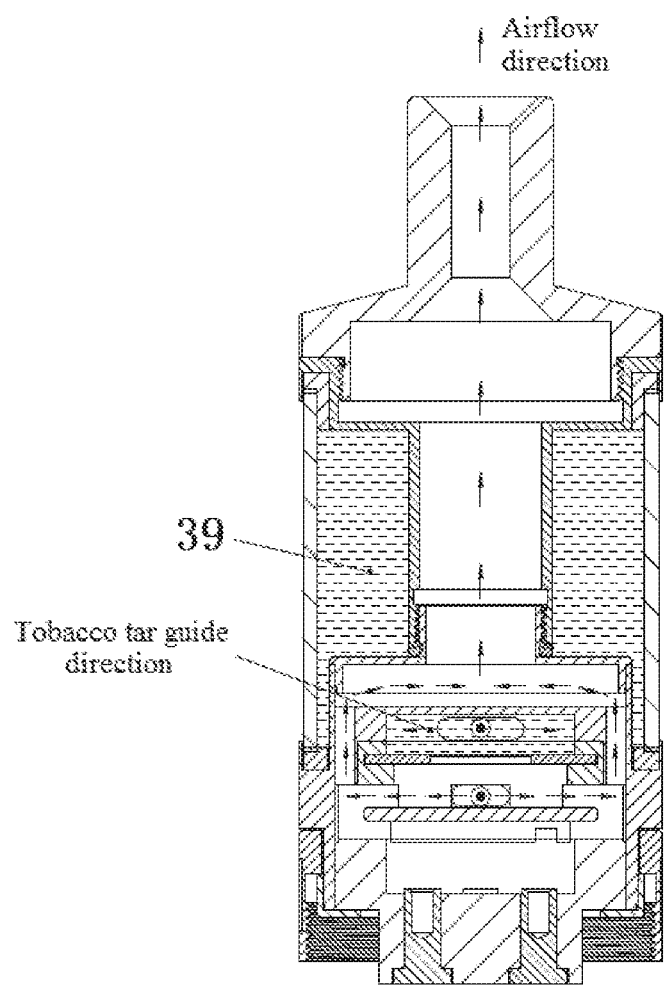
Figure 6:
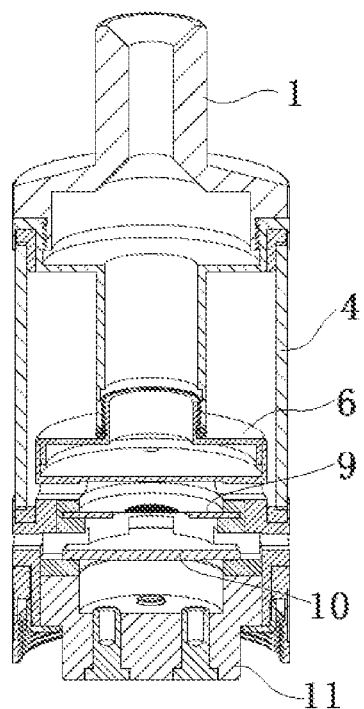
Figure 7:
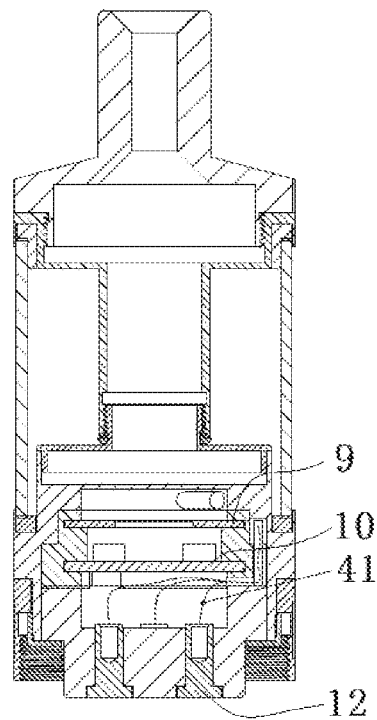

An electronic cigarette, comprising a battery component 50 and the combined ultrasonic atomizer, and the battery component 50 supplies power to the micropore atomization piece 9 and the high-frequency atomization piece 10. As shown in FIG. 3, the battery component 50 comprises a battery 54, an end cover 57 provided at the bottom of the battery 54, and a charging interface 55 and a charging PCB 56 both provided between the battery 54 and the end cover 57. An insulating base 51 is installed at the upper part of the battery 54, four electrode rings 58 are installed on the insulating base 51, and a key 59, a key PCB 52 and an electrode column 60 are both provided between the battery 54 and the insulating base 51. The electrode rings 58 of the battery component 50 are in electrical connection with four electrode rings 12 at the bottom of the ultrasonic atomizer. The battery 54 is provided with a battery casing 53, and the battery casing 53 connects the insulating base 51 with the end cover 57 to form an integral battery component. As shown in FIG. 3, the atomizer and the battery are locked and extruded by a locking ring with threads to form contact electric conduction. As shown in FIG. 7, the four electrode rings 12 installed on the insulating base 11 are respectively in electrical connection with the micropore atomization piece 9 and the high-frequency atomization piece 10 through corresponding conducting wires 41.

The embodiment has the beneficial effects that the integrated non-cotton atomization structure is free of the burnt flavor, free of tobacco tar soaking and has good taste.

Embodiment 2

As shown in FIG. 8 to FIG. 13, a combined ultrasonic atomizer, comprising a suction nozzle base 1, an upper end cover 2, a silica gel base 8 installed in the upper end cover 2, a high-frequency atomization piece 10 and a micropore atomization piece 9 both provided between the suction nozzle base 1 and the silica gel base 8, a tobacco tar bin 4, a sealing ring 3 provided between the upper end cover 2 and the tobacco tar bin 4, a lower end cover 19, a sealing ring 20 located between the tobacco tar bin 4 and the lower end cover 19, an insulating base 11 installed on the lower end cover 19 by a fixing ring 18, four electrode rings 12 installed on the insulating base 11, and a locking ring 13 for locking the insulating base 11 tightly on the lower end cover 19.

Figure 9:
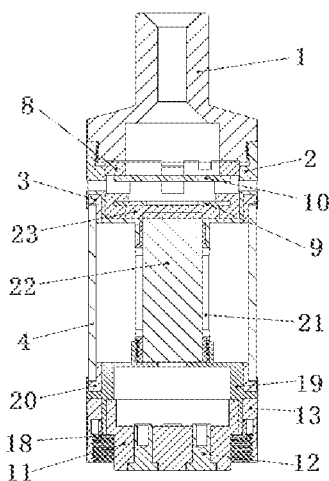
Figure 10:
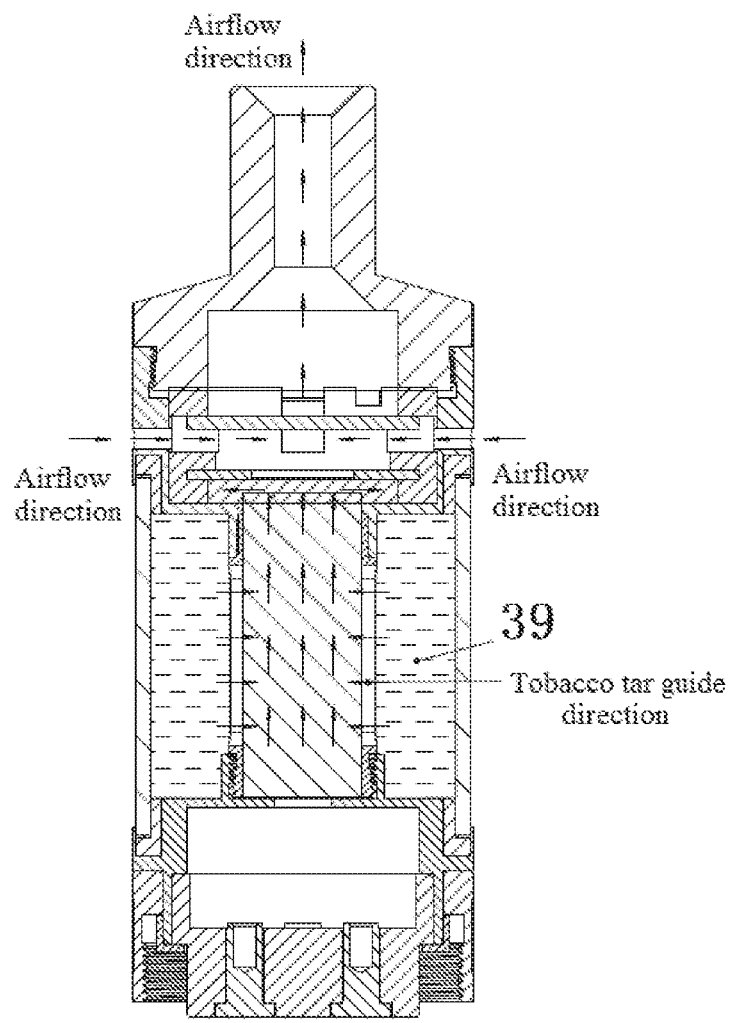
Figure 11:
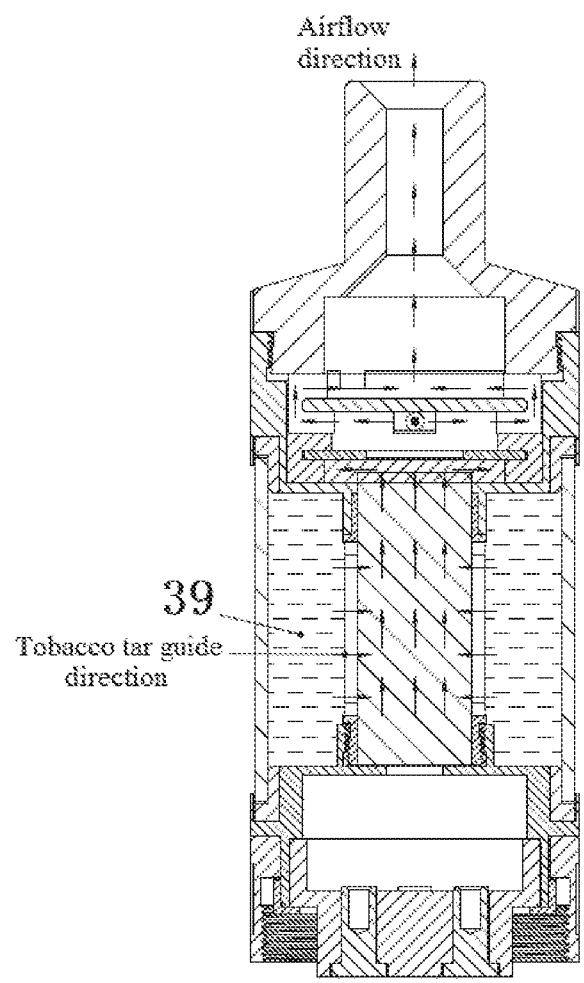
Figure 12:
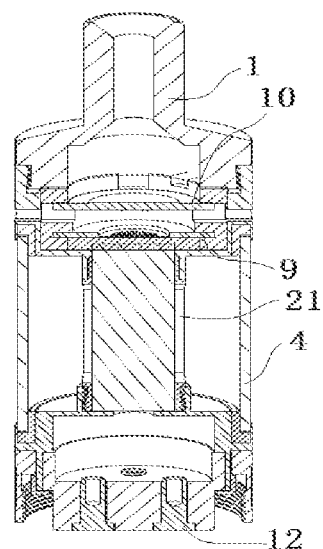

As shown in FIG. 9, a connecting ring 21 and tobacco tar guide cotton 22 sleeved in the connecting ring 21 are provided at the central position of the tobacco tar bin 4, and tobacco tar guide cotton 23 located in the silica gel base 8 is provided between the micropore atomization piece 9 and the upper end cover 2. As shown in FIG. 11, the high-frequency atomization piece 10 is located above the micropore atomization piece 9, and the micropore atomization piece 9 is in contact with the tobacco tar guide cotton.

Figure 8:
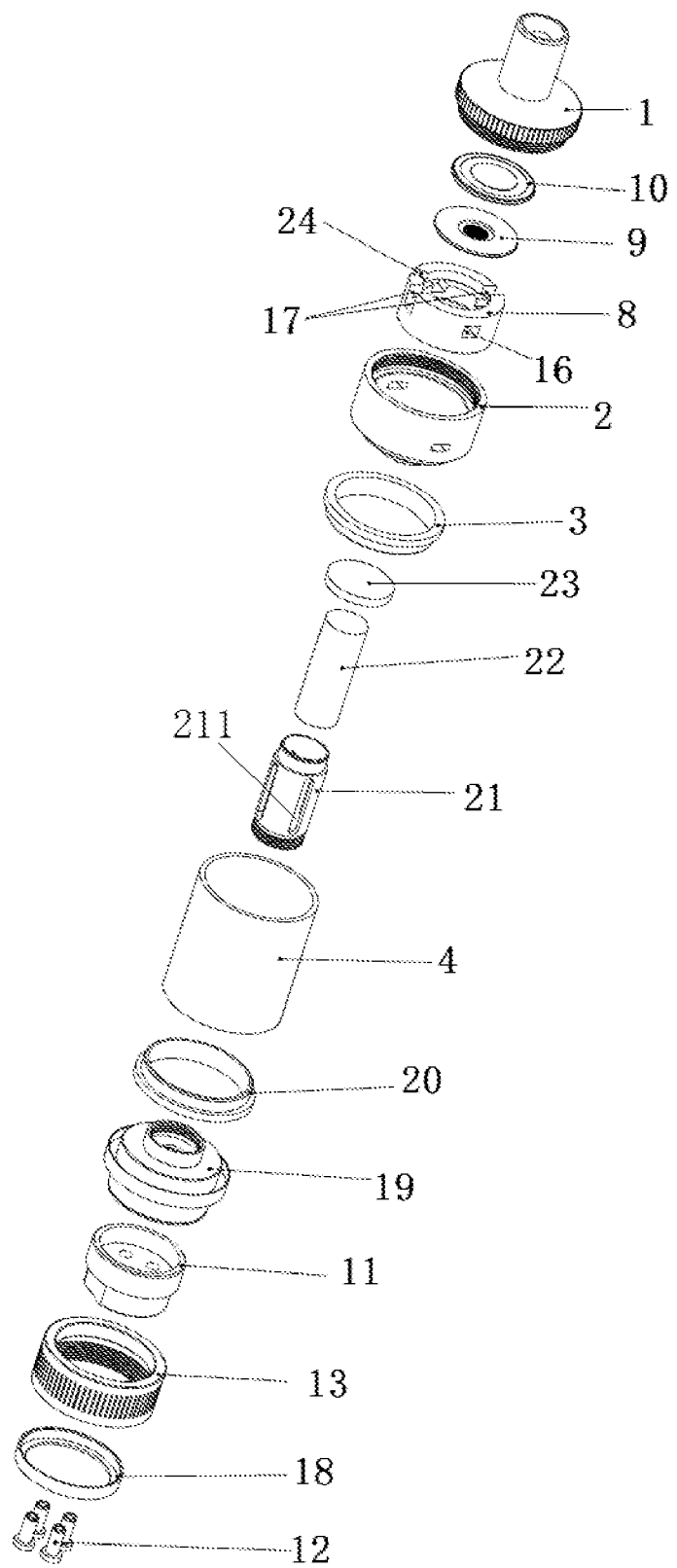

As shown in FIG. 8, an air inlet hole is provided in the side wall of the upper end cover 2, an air inlet hole 15 correspondingly communicating with the air inlet hole in the upper end cover is provided in the side wall of the silica gel base 8, and an air outlet groove 17 and a wire pass groove 24 are both provided in the top end of the side wall of the silica gel base 8. In a working process, the tobacco tar enters the micropore atomization piece 9 through the connecting ring 21, the tobacco tar guide cotton 22 and the tobacco tar guide cotton 23, the tobacco tar is oscillated and atomized by the micropore atomization piece 9 to form large-particle tobacco tar smoke with the particle size of 50-120-micron, the tobacco tar smoke is ejected to the lower surface of the high-frequency atomization piece 10 and is oscillated and atomized by the high-frequency atomization piece 10 to form small-particle tobacco tar smoke with the particle size of 70-130-micron, the air passes through the air inlet hole in the upper end cover and the air inlet hole 15 in the silica gel base 8 in sequence, and the atomized tobacco tar smoke is transferred to a hollow passage of the suction nozzle base by the air outlet groove 17 to be inhaled by the smoker.

Figure 13:
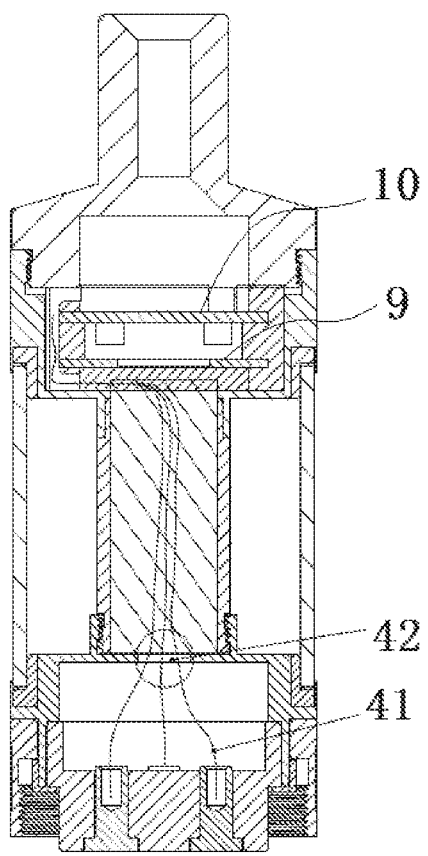
Figure 14:
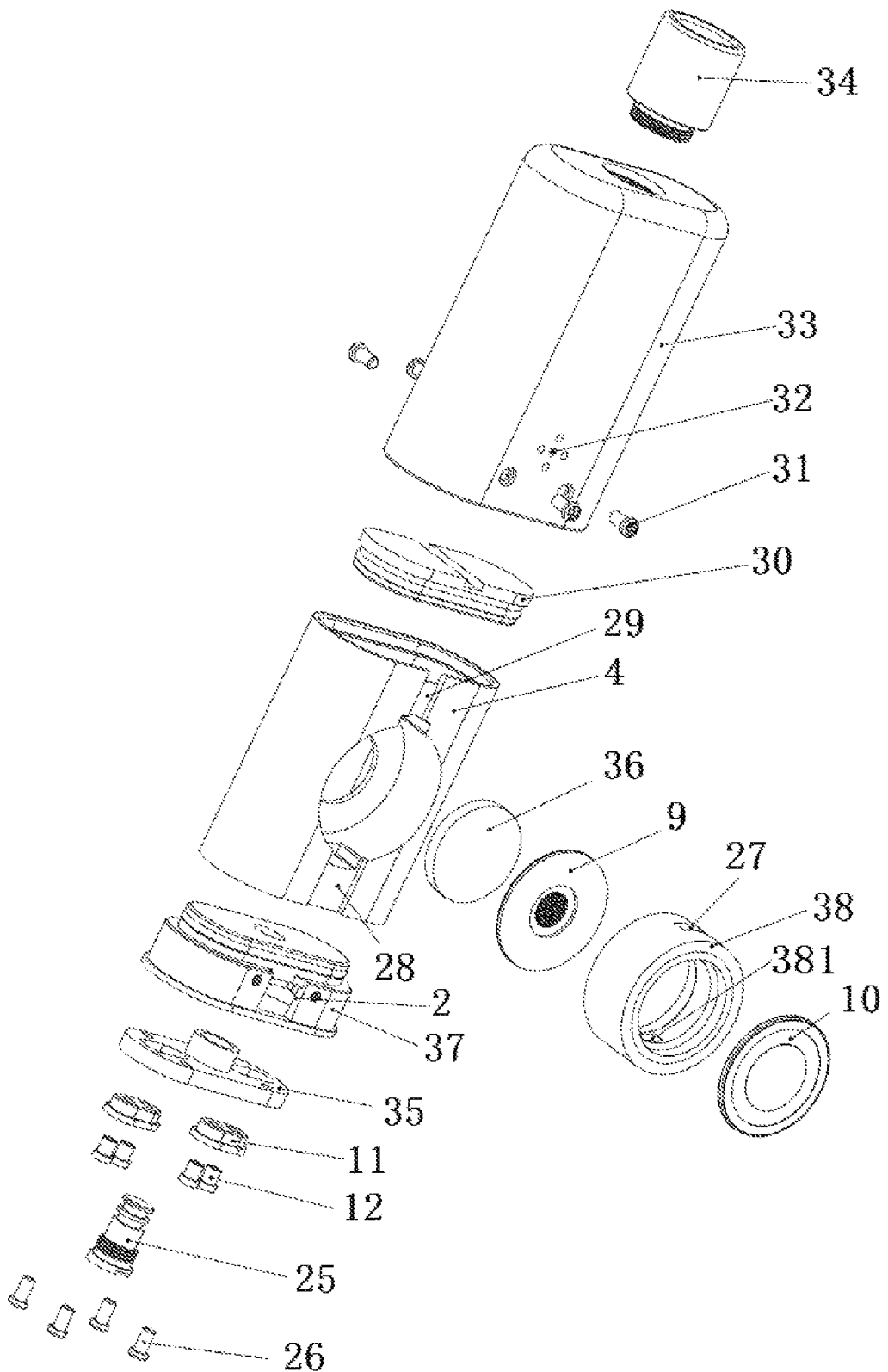
Figure 15:
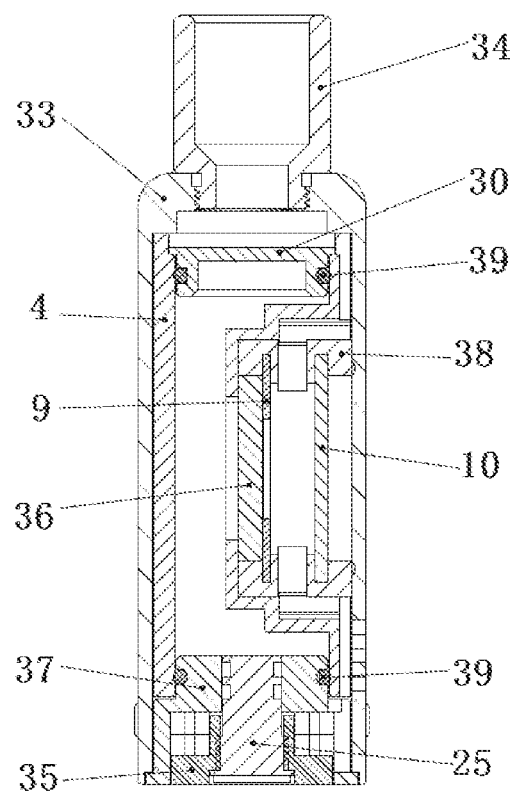

As shown in FIG. 13, the lower part of the insulating base 11 is flat which is used to be clamped in a corresponding flat position of the battery. Silica gel 42 for sealing the tobacco tar is coated on the joints of the top end of the lower end cover 19 and the connecting ring 21.

The differences between the embodiment 2 and the embodiment 1 are as follows:

1. the atomization pieces are provided at the top of the tobacco tar bin;

2. the two atomization pieces adopt inverted structures, the two atomization pieces are opposite to each other, that is the micropore atomization piece ejects the tobacco tar upward to the surface of the high-frequency atomization piece, and then the high-frequency atomization piece atomizes the tobacco tar; and 3. the micropore atomization piece firstly ejects the tobacco tar 39 upward to the atomization area of the micropore atomization piece using the tobacco tar guide cotton, and then the micropore ejects the tobacco tar to the high-frequency atomization piece for atomization; and 4. the air enters from the side face at the top, and then the air is discharged from the middle of the top of the suction nozzle, and the tobacco tar injection mode is the same as that in the embodiment 1.

The embodiment has the beneficial effects that the problem that the downward tobacco tar guide in the embodiment 1 might cause tobacco tar accumulation on the high-frequency atomization piece can be solved.

Embodiment 3

As shown in FIG. 14 to FIG. 19, a combined ultrasonic atomizer, comprising a suction nozzle 34, a housing 33, a tobacco tar bin 4 installed in the housing 33, bases 37 installed at bottom ends of the housing 33 and the tobacco tar bin 4, a tobacco tar injection plug 25 and four electrode rings 12 installed on a bottom cover 35 are installed on the base, each electrode ring is installed on the bottom cover 35 by one insulating base 11, and the bottom cover 35 is in detachable connection with the base 37 by a screw 26.

The top end of the tobacco tar bin 4 is in fixed connection with an upper end cover 30, an air inlet groove 28 is provided in the side wall of the lower end of the tobacco tar bin 4, an air outlet groove 29 is provided in the side wall of the upper end of the tobacco tar bin 4, a mounting hole is provided in the middle of the side wall of the tobacco tar bin 4, and tobacco tar guide cotton 36, a micropore atomization piece 9 a high-frequency atomization piece 10 are sequentially installed in the mounting hole from inside to outside; the micropore atomization piece 9 and the high-frequency atomization piece 10 are both fixed in a silica gel base 38, and the silica gel base is provided with an air inlet hole 381 correspondingly communicating with the air inlet groove and an air outlet hole 27 correspondingly communicating with the air outlet groove. The housing 33 is in fixed connection with the base 37 by a screw 31, and a plurality of air inlet holes 32 communicated with the air inlet groove 28 in the tobacco tar bin 4 are provided in the side wall of the housing 33.

Figure 16:
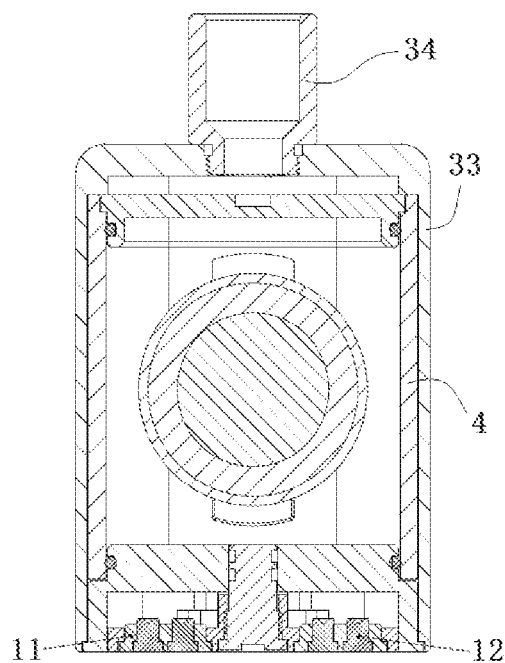
Figure 17:
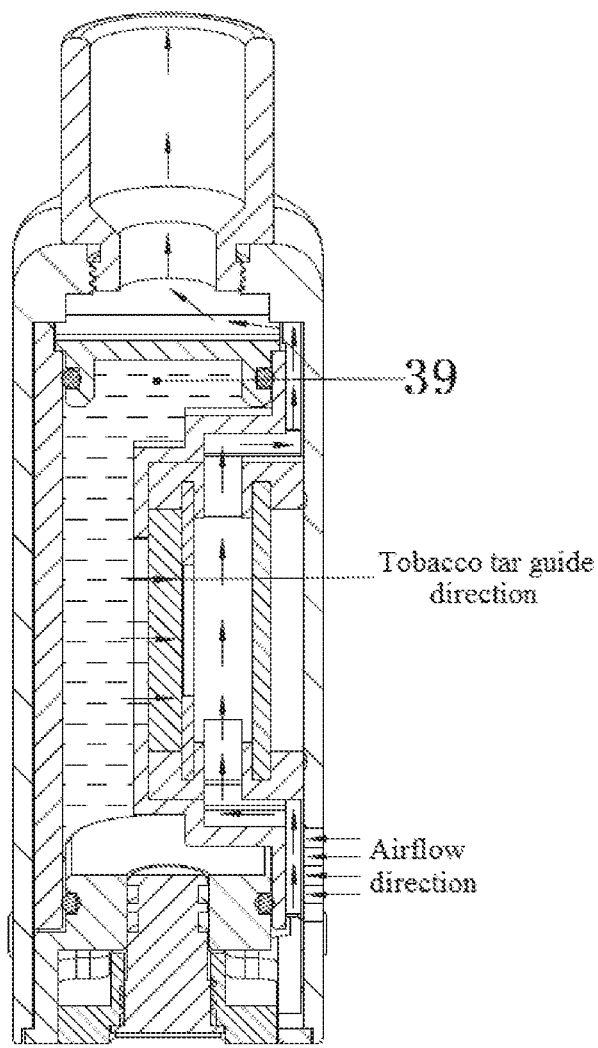
Figure 18:
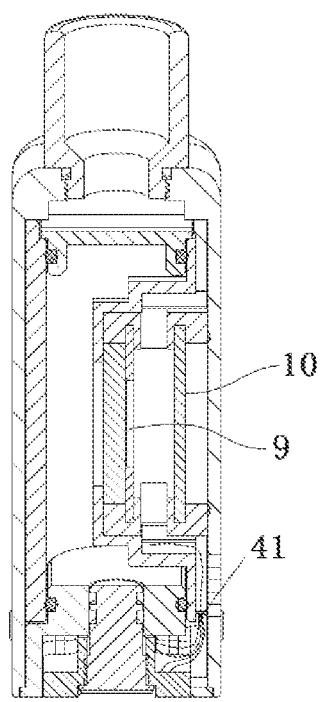
Figure 19:
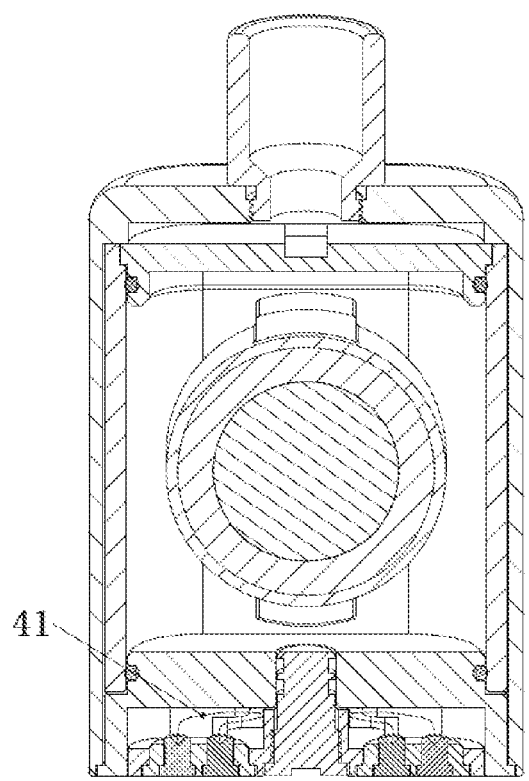

As shown in FIG. 16 and FIG. 17, the tobacco tar in the tobacco tar bin 4 permeates onto the micropore atomization piece 9 through tobacco tar guide cotton 36, the micropore atomization piece ejects atomized tobacco tar 39 onto the atomization surface of the high-frequency atomization piece 10, and the atomized tobacco tar smoke is transferred into the suction nozzle 34 through the air outlet hole 27 and the air outlet groove 29 to be inhaled by the smoker using the air passing through the air inlet groove 28 and the air inlet hole 81.

The difference between the embodiment 3 with the embodiment 1 and the embodiment 2 is as follows:

1. the atomization pieces are provided at the middle of the tobacco tar bin in a group, the two atomization pieces are vertically placed, the micropore atomization piece communicates with the tobacco tar bin, and the atomization surfaces of the two atomization pieces are opposite;

2. the tobacco tar is guided onto the micropore atomization piece by tobacco tar guide cotton, and the micropore atomization piece ejects the tobacco tar for high-frequency atomization;

3. the air enters from the side face of the bottom, and the air penetrates through the middle of the two atomization pieces to take the smoke out;

4. the tobacco tar injection hole is provided in the bottom and is sealed by a plug screw with a sealing ring, and the tobacco tar can be injected by unscrewing the plug screw; and 5. the atomizer and the battery are in contact electric conduction by absorption and compression between the magnets and the electrode rings.

The embodiment has the beneficial effects as follows: the tobacco tar accumulated on the surfaces of the two atomization pieces can flow downward because the atomization pieces are vertical placed, therefore the possible problem of tobacco tar accumulation of the high-frequency atomization piece can be solved, and the possible problem of tobacco tar accumulation of the micropore atomization piece can also be solved, accordingly the two atomization pieces can normally work very well.

The contents set forth in the above-mentioned embodiments should be construed in such a way that these embodiments are merely used for illustrating the present invention more clearly rather than limiting the scope of the present invention, and after reading the present invention, modifications in various equivalent forms made by those skilled in the art shall all fall within the scope limited by the claims appended in the present application.

The invention claimed is:

1. A combined ultrasonic atomizer, comprising a tobacco tar bin, an air inlet passage, a tobacco tar smoke outlet passage and an atomization component, characterized in that the atomization component comprises a micropore atomization piece used for performing first stage oscillation atomization on tobacco tar, and a high-frequency atomization piece used for performing second stage oscillation atomization on the tobacco tar; the micropore atomization piece is communicated with a tobacco tar outlet of the tobacco tar bin by direct contact or through a tobacco tar guide structure, and an ejection end of the micropore atomization piece faces an atomization surface of the high-frequency atomization piece; and the air inlet passage communicates with an atomization cavity located between the micropore atomization piece and the high-frequency atomization piece, and the atomization cavity communicates with the tobacco tar smoke outlet passage.

2. The combined ultrasonic atomizer of claim 1, wherein the micropore atomization piece and the high-frequency atomization piece are fixed to a silica gel base, and an air inlet hole or an air inlet groove communicated with the air inlet passage is provided in the silica gel base, and an air outlet hole or an air outlet groove communicated with the tobacco tar smoke outlet passage is provided in the silica gel base.

3. The combined ultrasonic atomizer of claim 1, wherein an outlet end of the tobacco tar smoke outlet passage communicates with a suction nozzle base.

4. The combined ultrasonic atomizer of claim 1, wherein the aperture of the micropore atomization piece is 40-100 microns, and the atomization surface of the high-frequency atomization piece is of solid structure.

5. The combined ultrasonic atomizer of claim 1, wherein the micropore atomization piece and the high-frequency atomization piece are horizontally provided below the tobacco tar bin, and the micropore atomization piece is located between the high-frequency atomization piece and the tobacco tar bin; and the tobacco tar outlet of the tobacco tar bin directly communicates with the upper end face of the micropore atomization piece.

6. The combined ultrasonic atomizer of claim 5, wherein an air corridor for communicating the upper end with the lower end is provided at the central position of the tobacco tar bin, and the air corridor communicates with the atomization cavity to form the tobacco tar smoke outlet passage.

7. The combined ultrasonic atomizer of claim 5, wherein the lower end of the tobacco tar bin is connected with a base, and the silica gel base for fixing the micropore atomization piece and the high-frequency atomization piece is installed in the base; the base is provided with a tobacco tar inlet hole and an air inlet hole, and an air inlet groove and an air outlet groove are provided in the silica gel base; and the air inlet hole in the base correspondingly communicates with the air inlet groove in the silica gel base to form the air inlet passage.

8. The combined ultrasonic atomizer of claim 7, wherein the lower end of the base is connected with an insulating base, and an electrode ring is installed on the insulating base, and the micropore atomization piece and the high-frequency atomization piece are respectively in electrical connection with the electrode ring through conducting wires.

9. The combined ultrasonic atomizer of claim 1, wherein the micropore atomization piece and the high-frequency atomization piece are horizontally provided above the tobacco tar bin, and the micropore atomization piece is located between the high-frequency atomization piece and the tobacco tar bin; and the tobacco tar outlet of the tobacco tar bin communicates with the lower end face of the micropore atomization piece through tobacco tar guide cotton.

10. The combined ultrasonic atomizer of claim 9, wherein a connecting ring for communicating the upper end with the lower end is provided at the central position of the tobacco tar bin, the tobacco tar guide cotton is provided in the connecting ring, and the tobacco tar guide cotton is provided at the top end of the connecting ring; and a plurality of tobacco tar pass holes are provided in the wall surface of the connecting ring.

11. The combined ultrasonic atomizer of claim 9, wherein an upper end cover is installed at the top end of the tobacco tar bin, and the silica gel base for fixing the micropore atomization piece and the high-frequency atomization piece is installed in the upper end cover; the upper end cover is provided with an air inlet hole; an air inlet hole and an air outlet groove are provided in the silica gel base; and the air inlet hole of the upper end cover correspondingly communicates with the air inlet hole of the silica gel base to form the air inlet passage.

12. The combined ultrasonic atomizer of claim 10, wherein the air outlet groove is provided in the top end of the side wall of the silica gel base, and the air outlet groove communicates with the atomization cavity to serve as the tobacco tar smoke outlet passage.

13. The combined ultrasonic atomizer claim 1, wherein the micropore atomization piece and the high-frequency atomization piece are vertically provided on one side of the tobacco tar bin, and the micropore atomization piece is located between the high-frequency atomization piece and the tobacco tar bin; and the tobacco tar outlet of the tobacco tar bin communicates with the inner end face of the micropore atomization piece through tobacco tar guide cotton.

14. The combined ultrasonic atomizer of claim 13, wherein a mounting hole is provided in the side wall of the tobacco tar bin, and the silica gel base for fixing the micropore atomization piece and the high-frequency atomization piece is installed in the mounting hole; an air inlet hole and an air outlet hole are provided in the side wall of the silica gel base; and an air inlet groove and an air outlet groove are provided in the side wall of the tobacco tar bin; and the air inlet hole in the silica gel base correspondingly communicates with the air inlet groove in the tobacco tar bin to form the air inlet passage communicated with the atomization cavity, and the air outlet hole in the silica gel base correspondingly communicates with the air outlet groove in the tobacco tar bin to form the tobacco tar smoke outlet passage communicated with the atomization cavity.

15. The combined ultrasonic atomizer of claim 14, wherein the tobacco tar bin is provided in a housing, and an air inlet hole communicated with the air inlet groove in the tobacco tar bin is provided in the side wall of the housing.

16. An electronic cigarette, wherein the electronic cigarette comprises a battery component and the combined ultrasonic atomizer of claim 1, the battery component respectively supplies power to the micropore atomization piece and the high-frequency atomization piece.

17. The electronic cigarette of claim 16, wherein the battery component comprises a battery, an insulating base installed at the top end of the battery, an electrode column and an electrode ring both installed in the insulating base which are conducted with the battery; and the electrode ring is in electrical connection with the micropore atomization piece and the high-frequency atomization piece through conducting wires respectively.

18. A method for atomizing tobacco tar by using the combined ultrasonic atomizer of claim 1, wherein the method comprises the following steps:
   S1, transferring the tobacco tar in the tobacco tar bin onto the micropore atomization piece directly or through the tobacco tar guide structure to perform oscillation atomization;
   S2, ejecting the tobacco tar on the micropore atomization piece after oscillation atomization onto the atomization surface of the high-frequency atomization piece to perform secondary atomization; and
   S3, transferring the tobacco tar smoke produced by the secondary atomization of the high-frequency atomization piece to the suction nozzle through the air outlet passage using the air entered from the air inlet passage of the ultrasonic atomizer.

19. The method for atomizing tobacco tar of claim 18, wherein in step S1, the aperture of the micropore atomization piece is 40-100 microns, the vibration frequency of the micropore atomization piece is 100-200 KHZ, and the particle size of the tobacco tar smoke after atomization is 50-120 microns.

20. The method for atomizing tobacco tar of claim 18, wherein in step S2, the atomization surface of the high-frequency atomization piece is of solid structure, the vibration frequency of the high-frequency atomization piece is 1-3 MHZ, and the particle size of the tobacco tar smoke after atomization is 70-130 nanometers.

* * * * *